(12) United States Patent
DiMino et al.

(10) Patent No.: US 11,071,876 B2
(45) Date of Patent: Jul. 27, 2021

(54) APPARATUS AND METHOD FOR TREATMENT OF MENTAL AND BEHAVIORAL CONDITIONS AND DISORDERS WITH ELECTROMAGNETIC FIELDS

(71) Applicant: AAH HOLDINGS LLC, Pinehurst, NC (US)

(72) Inventors: Andre' A. DiMino, Woodcliff Lake, NJ (US); Matthew Drummer, Fort Lee, NJ (US); Judy Korman, Mill Spring, NC (US); Francis J. Russo, Glen Head, NY (US)

(73) Assignee: AAH HOLDINGS LLC, Pinhurst, NC (US)

( * ) Notice: Subject to any disclaimer, the term of this patent is extended or adjusted under 35 U.S.C. 154(b) by 20 days.

(21) Appl. No.: 16/702,020

(22) Filed: Dec. 3, 2019

(65) Prior Publication Data

US 2020/0171318 A1  Jun. 4, 2020

Related U.S. Application Data

(60) Provisional application No. 62/774,593, filed on Dec. 3, 2018.

(51) Int. Cl.
*A61N 2/02* (2006.01)
*A61N 2/00* (2006.01)
*A01K 27/00* (2006.01)

(52) U.S. Cl.
CPC ............ *A61N 2/006* (2013.01); *A01K 27/002* (2013.01); *A01K 27/009* (2013.01); *A61N 2/02* (2013.01)

(58) Field of Classification Search
CPC .................................. A61N 2/006; A61N 2/02
See application file for complete search history.

(56) References Cited

U.S. PATENT DOCUMENTS

| 4,556,051 A | 12/1985 | Maurer |
| 5,565,005 A | 10/1996 | Erickson et al. |

(Continued)

FOREIGN PATENT DOCUMENTS

| CN | 101160152 A | 4/2008 |
| CN | 101415462 A | 4/2009 |

(Continued)

OTHER PUBLICATIONS

Assisi "Loop Proven Science. Positive Results" Product Catalogue [online] Apr. 26, 2018. Retrieved Jan. 27, 2020. Retrieved from the internet: <URL: http://web.archive.org/web/20180426060128/http://www.assisianimalhealth.com/product/>.

(Continued)

*Primary Examiner* — Christine H Matthews
(74) *Attorney, Agent, or Firm* — Amsler, Rothstein & Ebenstein LLP (57) ABSTRACT

An apparatus for treating a behavioral condition of an animal, including a loop coil; a signal generator coupled to the loop coil, the signal generator being configured to transmit a treatment signal through the loop coil; and a harness connected to one or more of the loop coil and the signal generator, the harness including one or more fasteners each configured to fasten to one or more of a neck and a forelimb joint of the animal to position the loop coil proximate a head of the animal, the treatment signal including a plurality of bursts having a peak amplitude of less than about 200 milliGauss, the plurality of bursts having an average duration of between about 0.5 msec and about 50 msec, and the plurality of bursts being repeated at between 0.01 and 100 Hz.

14 Claims, 3 Drawing Sheets

(56) References Cited

U.S. PATENT DOCUMENTS

| | | |
|---|---|---|
| 5,584,863 A | 12/1996 | Conyers et al. |
| 5,723,001 A | 3/1998 | Pilla et al. |
| 5,766,231 A | 6/1998 | Erickson et al. |
| 7,611,453 B2 | 11/2009 | Pilla et al. |
| 7,740,574 B2 | 6/2010 | Pilla |
| 7,744,524 B2 | 6/2010 | Pilla |
| 7,758,490 B2 | 7/2010 | Pilla |
| 7,783,348 B2 | 8/2010 | Gill et al. |
| 7,896,797 B2 | 3/2011 | Pilla |
| 8,343,027 B1 | 1/2013 | DiMino et al. |
| 8,415,123 B2 | 4/2013 | Pilla |
| 8,768,454 B2 | 7/2014 | Sham et al. |
| 8,961,385 B2 | 2/2015 | Pilla et al. |
| 9,320,913 B2 | 4/2016 | DiMino et al. |
| 9,352,167 B2 | 5/2016 | Schneider |
| 9,381,374 B2 | 7/2016 | Mishelevich et al. |
| 9,387,339 B2 | 7/2016 | Sham et al. |
| 9,410,143 B1 | 8/2016 | Rudd |
| 9,415,233 B2 | 8/2016 | Pilla et al. |
| 9,427,598 B2 | 8/2016 | Pilla et al. |
| 9,433,797 B2 | 9/2016 | Pilla et al. |
| 9,440,089 B2 | 9/2016 | Pilla et al. |
| 9,492,679 B2 | 11/2016 | Schneider et al. |
| 9,656,096 B2 | 5/2017 | Pilla |
| 9,849,299 B2 | 12/2017 | Sham et al. |
| 9,968,797 B2 | 5/2018 | Sham et al. |
| 10,556,121 B2 | 2/2020 | Gurfein |
| 2005/0182287 A1* | 8/2005 | Becker .................... A61N 2/02 600/13 |
| 2005/0251229 A1 | 11/2005 | Pilla et al. |
| 2006/0212077 A1 | 9/2006 | Pilla et al. |
| 2007/0026514 A1 | 2/2007 | Pilla et al. |
| 2007/0173904 A1 | 7/2007 | Pilla |
| 2007/0300140 A1 | 12/2007 | Makela et al. |
| 2008/0058793 A1 | 3/2008 | Pilla et al. |
| 2008/0132971 A1 | 6/2008 | Pilla et al. |
| 2008/0140155 A1 | 6/2008 | Pilla et al. |
| 2010/0210893 A1 | 8/2010 | Pilla |
| 2010/0222631 A1 | 9/2010 | Pilla |
| 2011/0112352 A1 | 5/2011 | Pilla et al. |
| 2012/0089201 A1 | 4/2012 | Pilla et al. |
| 2013/0218235 A9 | 8/2013 | Pilla |
| 2013/0274540 A1 | 10/2013 | Pilla |
| 2014/0046117 A1 | 2/2014 | Pilla et al. |
| 2014/0046232 A1 | 2/2014 | Sham et al. |
| 2014/0213843 A1 | 7/2014 | Pilla et al. |
| 2014/0303425 A1 | 10/2014 | Pilla et al. |
| 2015/0196771 A1 | 7/2015 | Pilla et al. |
| 2015/0217126 A1 | 8/2015 | Pilla |
| 2016/0121135 A1 | 5/2016 | Pilla |
| 2017/0080245 A1 | 3/2017 | DiMino et al. |
| 2017/0186346 A1 | 6/2017 | McNeal et al. |
| 2020/0044318 A1 | 2/2020 | Pilla et al. |
| 2020/0094068 A1 | 3/2020 | DiMino et al. |

FOREIGN PATENT DOCUMENTS

| | | |
|---|---|---|
| CN | 101444074 A | 5/2009 |
| CN | 1980610 A | 5/2010 |
| CN | 1901967 B | 12/2011 |
| CN | 101432041 B | 4/2012 |
| CN | 104023790 A | 9/2014 |
| CN | 107641636 A | 1/2018 |
| EP | 3 272 854 A1 | 1/2018 |
| JP | 2018-007647 A | 1/2018 |
| KR | 20180009985 A | 1/2018 |
| WO | 1995/33514 A1 | 12/1995 |
| WO | 200505611 A2 | 6/2005 |
| WO | 2005102188 A1 | 11/2005 |
| WO | 2013067512 A1 | 5/2013 |
| WO | 2018208673 A1 | 11/2018 |

OTHER PUBLICATIONS

International Search Report received for PCT Patent Application No. PCT/US2019/064218, dated Feb. 18, 2020, 3 pages.

Written Opinion received for PCT Patent Application No. PCT/US2019/064218, completed on Jan. 30, 2020, 12 pages.

Pilla et al., "EMF signals and ion/ligand binding kinetics: prediction of bioeffective waveform parameters," Bioelectrochemistry and Bioenergetics, vol. 48, Issue 1, pp. 27-34, Feb. 1999.

* cited by examiner

Figure 3

APPARATUS AND METHOD FOR TREATMENT OF MENTAL AND BEHAVIORAL CONDITIONS AND DISORDERS WITH ELECTROMAGNETIC FIELDS

CROSS-REFERENCE TO RELATED APPLICATION

The present application claims the benefit of and priority to U.S. Provisional Patent Application No. 62/774,593, filed on Dec. 3, 2018, the entire contents of which are incorporated by reference herein

FIELD OF THE INVENTION

This invention pertains generally to an electromagnetic treatment coil apparatus and a method for using same to achieve modification of mental and behavioral conditions and disorders by application of encoded electromagnetic signals. More particularly, this invention relates to the application, by surgically non-invasive coupling, of highly specific electromagnetic signal patterns to the head or skull for inductive treatment of neurological and brain tissue and cells. This invention also relates to treatment of living tissues and cells by altering their interaction with their electromagnetic environment. The invention further relates to a method of modification of cellular and tissue growth, repair, maintenance, and general behavior by the application of encoded electromagnetic information. An embodiment according to the present invention pertains to use of non-thermal, time-varying magnetic fields to target pathway structures, such as molecules, cells, tissue, and organs. Use of the below specified electromagnetic waveforms produced by the inventive method and apparatus can have particular utility in the treatment of anxiety in humans and animals. The invention disclosed herein is a non-invasive, non-pharmacological treatment modality that can have a significant salutary impact on persons or animals suffering from these conditions or disorders or that can be used on a prophylactic basis for those subjects that may be prone to these conditions or disorders. An embodiment according to the present invention pertains to using an induction means, such as an applicator coil, to deliver pulsed electromagnetic fields ("PEMF") for the treatment of neurological and brain structures, tissues, and cells. The instant invention describes the use of specific encoded electromagnetic signals to augment release of growth factors and cytokines related to the treatment of inflammatory processes causing mental and behavioral conditions and disorders, as well as other physiological and biochemical factors contributing to mental and behavioral conditions and disorders.

BACKGROUND OF THE INVENTION

It is now well established that application of weak non-thermal electromagnetic fields ("EMF") can result in physiologically meaningful in-vivo and in-vitro bioeffects. EMF has been used in applications of bone repair and bone healing. Waveforms comprising low frequency components and low power are currently used in orthopedic clinics. Origins of using bone repair signals began by considering that an electrical pathway may constitute a means through which bone can adaptively respond to EMF signals. A linear physiochemical approach employing an electrochemical model of a cell membrane predicted a range of EMF waveform patterns for which bioeffects might be expected. Since a cell membrane was a likely EMF target, it became necessary to find a range of waveform parameters for which an induced electric field could couple electrochemically at the cellular surface, such as voltage-dependent kinetics. Extension of this linear model also involved Lorentz force analysis (see, e.g., Pilla et al., *Gap junction impedance tissue dielectrics and thermal noise limits for electromagnetic field bioeffects*, Bioelectrochemistry and Bioenergetics, vol. 35, pp. 63-69 (November 1994).)

A pulsed radio frequency (PRF) signal derived from a 27.12 MHz continuous sine wave used for deep tissue healing is known in the prior art of diathermy. A pulsed successor of the diathermy signal was originally reported as an EMF capable of eliciting a non-thermal biological effect in the treatment of infections in Ginsberg, A. J., *Ultrashort radio waves as a therapeutic agent*, Med Record 140, 651-653 (Dec. 19, 1934). Since that original work, PRF therapeutic applications have been reported for the reduction of post-traumatic and post-operative pain and edema in soft tissues, wound healing, burn treatment, and nerve regeneration. The application of EMF for the resolution of traumatic edema has become increasingly used in recent years. Results, to date, using PRF in animal and clinical studies suggest that pain and edema may be measurably reduced from such electromagnetic stimulus.

The present invention is based upon biophysical and animal studies which attribute the effect of cell-to-cell communication on the sensitivity of tissue structures to induced voltages and associated currents. These studies have established that prior art considerations of EMF dosimetry have not taken into account the dielectric properties of tissue structure (as opposed to the properties of isolated cells). The implications thereof are that a proper, i.e., an efficient, reactive coupling of an EMF signal to tissue for the purpose of treating the head and cerebral tissue related to migraine and sinus headaches is referenced in the prior art (see U.S. Pat. No. 9,440,089) The use of an efficient, reactive coupling of specific EMF signals to neurological and brain structures, tissues, and cells for the purpose of treating mental and behavioral conditions and disorders has not heretofore been effected in the art of record.

Cellular studies have addressed effects of weak low-frequency electromagnetic fields on both signal transduction pathways and growth factor synthesis. It can be shown that EMF stimulates secretion of growth factors after a short, trigger-like duration. Ion/ligand binding processes at a cell membrane are generally considered an initial EMF target pathway structure. The clinical relevance to treatments, for example, of bone repair, is upregulation such as modulation, of growth factor production as part of normal molecular regulation of bone repair. Cellular level studies have shown effects on calcium ion transport, cell proliferation, Insulin Growth Factor-II ("IGF-II") release, and IGF-II receptor expression in osteoblasts. Effects on IGF-I and II have also been demonstrated in rat fracture callus. Stimulation of transforming growth factor beta ("TGF-β") messenger RNA ("mRNA") with PEMF in a bone induction model in a rat has been shown. Studies have also demonstrated upregulation of TGF-β mRNA by PEMF in human osteoblast-like cell line designated MG-63, wherein there were increases in TGF-β1, collagen, and osteocalcin synthesis. PEMF stimulated an increase in TGF-β1 in both hypertrophic and atrophic cells from human non-union tissue. Further studies demonstrated an increase in both TGF-β1 mRNA and protein in osteoblast cultures resulting from a direct effect of EMF on a calcium/calmodulin (Ca/CaM)-dependent pathway. Cartilage cell studies have shown similar increases in TGF-β1 mRNA and protein synthesis from EMF, demonstrating a therapeutic application to joint repair.

According to the Anxiety and Depression Association of America ("ADAA"), anxiety disorders are the most common mental illness in the U.S., affecting 40 million adults in the United States age 18 and older, or 18.1% of the population every year. People with an anxiety disorder are three to five times more likely to go to the doctor and six times more likely to be hospitalized for psychiatric disorders than those who do not suffer from anxiety disorders. With respect to animals, of the over 75 million dogs in the US, it has been estimated that up to 39% suffer from at least one anxiety or fear issue (*Prevalence, comorbidity and behavioral variation in canine anxiety*, Tiira, et al; Journal of Veterinary Behavior 16 (2016) 36-44) with owners spending in excess of over $1 Billion each year dealing with such issues. Recent industry publications report that in a 2-year period, veterinarians have reported an increase in euthanasia due to unresolved behavior issues (source: PDSA (The People's Dispensary for Sick Animals, UK) PAW report 2015).

When a stressful event is experienced, whether imagined or actual, the amygdala, an area of the brain that contributes to emotional processing, sends a distress signal to the hypothalamus. The hypothalamus communicates with the rest of the body through the autonomic nervous system, which controls such involuntary body functions as breathing, blood pressure, heartbeat, and the dilation or constriction of key blood vessels and small airways in the lungs called bronchioles. The autonomic nervous system has two components, the sympathetic nervous system and the parasympathetic nervous system. The sympathetic nervous system triggers the fight-or-flight response, providing the body with a burst of energy so that it can respond to perceived dangers. The parasympathetic nervous system promotes the "rest and digest" response that calms the body down after the danger has passed.

After the amygdala sends a distress signal, the hypothalamus activates the sympathetic nervous system by sending signals through the autonomic nerves to the adrenal glands. These glands respond by pumping the hormone epinephrine (also known as adrenaline) into the bloodstream. As epinephrine circulates through the body, it brings on a number of physiological changes. The heart beats faster than normal, pushing blood to the muscles, heart, and other vital organs. Pulse rate and blood pressure go up and breathing is more rapid. Small airways in the lungs open wide. This way, the lungs can take in as much oxygen as possible with each breath. Extra oxygen is sent to the brain, increasing alertness. Sight, hearing, and other senses become sharper. Meanwhile, epinephrine triggers the release of blood sugar (glucose) and fats from temporary storage sites in the body. These nutrients flood into the bloodstream, supplying energy to all parts of the body.

All of these changes happen quickly, the amygdala and hypothalamus start this cascade even before the brain's visual centers have had a chance to fully process what is happening.

As the initial surge of epinephrine subsides, the hypothalamus activates the second component of the stress response system—known as the hypothalamic pituitary adrenal (HPA) axis. This network consists of the hypothalamus, the pituitary gland, and the adrenal glands.

The HPA axis relies on a series of hormonal signals to keep the sympathetic nervous system active. If the brain continues to perceive something as dangerous, the hypothalamus releases corticotropin-releasing hormone (CRH), which travels to the pituitary gland, triggering the release of adrenocorticotropic hormone (ACTH). This hormone travels to the adrenal glands, prompting them to release cortisol. The body thus stays revved up and on high alert. When the threat passes, cortisol levels fall. The parasympathetic nervous system then dampens the stress response.

SUMMARY OF THE INVENTION

Stress factors have been identified in a neuronal inflammatory response (Furuyashiki, T. et. al, Neural inflammation plays critical role in stress-induced depression, Kobe Univer. Jul. 18, 2018). Inflammation is affected by the body in the Calcium/Calmodulin (Ca/CaM) binding mechanism through the Ca dependent nitric oxide (NO) cascade, as the body attempts to control the cascade.

In light of the above, it is an object of the present invention to affect the inflammatory mechanism in order to alleviate neurological stress responses.

According to an exemplary embodiment of the invention, a PEMF signal may be used to increase NO to enhance Ca/CaM binding and thereby reduce inflammation. PEMF signals produced in accordance with exemplary embodiments of the invention have proven to stimulate endogenous NO production. Increased NO production has been shown to initiate neuroprotective signaling cascades. (Casper, D. et. al PEMF Potentiates the Induction of Nitric Oxide by Glutamate and 6-Hydroxydopamine in a Neuronal Cell Line, Bioem, 2009). The research concluded that there was a rapid effect from the PEMF signals on NO synthesis in a neuronal cell line with a 10-fold increase in NO levels (Casper et al., BEMS, Davos, 2009, P-20).

This invention comprises an apparatus and a method for delivering electromagnetic signals to human and animal target pathway structures, such as molecules, cells, tissue and organs, for the treatment of inflammatory and other contributing neuronal activity thereby positively affecting mental and behavioral conditions and disorders in humans and animals.

According to an exemplary embodiment of the invention, a PEMF treatment signal generator apparatus incorporates miniaturized circuitry and lightweight flexible coils in a wearable assembly for treating a human or animal. This advantageously allows a device to be completely portable and if desired to be constructed as disposable or reusable for the treatment of humans and animals with such mental and behavioral conditions and disorders.

The present invention is based upon the hypothesis that a pulse burst envelope of higher spectral density can more efficiently couple to physiologically relevant dielectric pathways, such as cellular membrane receptors, ion binding to cellular enzymes, and general transmembrane potential changes. In other words, the instant invention developed from the concept that, by the use of a burst duration which is generally below 100 microseconds for each PRF burst, one was limiting the frequency components that could couple to the relevant dielectric pathways in cells and tissue and, accordingly, that by increasing the number of frequency components transmitted to relevant cellular pathways, one would gain access to a larger range of biophysical phenomena applicable to known healing mechanisms, including enhanced enzyme activity and growth factor and cytokine release. The instant invention is, accordingly, the result of the discovery by the inventors that by increasing the burst duration and by applying a pseudo-random, or other high spectral density envelope, to the pulse burst envelope of mono- or bi-polar rectangular or sinusoidal pulses, which induce peak electric fields between $10^{-6}$ and 10 V/cm, a more efficient and greater effect could be achieved on biological healing processes with particular utility in the treatment of the processes which cause mental and behavioral conditions and disorders.

As a particular consequence of the approach of the instant invention, it has been discovered that by applying a high spectral density voltage envelope as the modulating or pulse-burst defining parameter, the power requirement for such increased duration pulse bursts can be significantly lower than that of shorter pulse bursts containing pulses within the same frequency range; this is due to more efficient matching of the frequency components to the relevant cellular/molecular process. Accordingly, the dual advantages of enhanced transmitted dosimetry to the relevant dielectric pathways and of decreased power requirement are achieved. This allows for the implementation of the present invention in an easily transportable unit for ease of application to the head and neck area of humans and animals.

The apparatus according to the instant invention allows the application of specific waveforms in a convenient and comfortable configuration to the targeted head and neck area. In one embodiment of the apparatus, a portable generator with a coil applicator is incorporated into a flexible fabric holder or harness worn by the user during a posteriori or prophylactic treatment of mental or behavioral conditions or disorders, such as anxiety. This allows for the proper positioning of the output coil to the targeted treatment area thereby allowing the produced signals to be broadcast over the brain in an efficient manner.

A method for treating a mental or behavioral condition or disorder in a human or animal subject in need thereof, the method comprising: placing a pulsed electromagnetic device comprising a pulsed electromagnetic field source external to a patient's head and in proximity to a target region for treatment through the skull; generating a pulsed electromagnetic field from the pulsed electromagnetic field source wherein the pulsed electromagnetic field comprises bursts of between 15-40 MHz sinusoidal waves, wherein the bursts repeat at between 0.01 and 100 Hz; applying the pulsed electromagnetic field through the skull to the target region; and reducing a physiological response to the mental or behavioral neurological condition or disorder by applying the pulsed electromagnetic field, wherein the pulsed electromagnetic field has a strength of 200 milliGauss or less.

It is, accordingly, an object of the invention to provide an improved electromagnetic method of the beneficial treatment of living cells and tissue by the modulation of electromagnetically sensitive regulatory processes at the cell membrane and at junctional interfaces between cells for the treatment of mental or behavioral conditions or disorders.

It is another object to provide an electromagnetic treatment method of the above type having a broad-band, high spectral density electromagnetic field.

It is a further object of the invention to provide a method of the above type in which amplitude modulation of the pulse burst envelope of the electromagnetic signal will induce coupling with a maximum number of relevant EMF-sensitive pathways in cells or tissues.

It is an object of the present invention to provide a method and apparatus for therapeutically treating humans and animals using electromagnetic fields selected by optimizing a power spectrum of a waveform to be applied to a chosen biochemical target pathway structure, such as a molecule, cell, tissue and organ.

It is a further object of the present invention to deliver a waveform configured according to the present invention for a treatment session of 1 minute to 6 hours duration.

It is yet another object of the present invention to automatically deliver a waveform configured according to the present invention following a predefined regimen by which PEMF treatment may be applied for a selected number of daily sessions, varied daily according to a predefined treatment protocol.

It is a further object of the present invention to deliver a waveform designed to modulate ion and ligand binding to molecules in physiological fluids and living cells and tissues.

It is yet a further object of the present invention to deliver a waveform configured to modulate calcium binding to calmodulin.

It is another object of the invention to provide an improved method of enhancing soft tissue and hard tissue repair.

It is another object of the invention to provide an improved method of increasing blood flow to affected tissues by modulating angiogenesis, vascularogenesis, and neovasculasization.

It is another object of the invention to provide an electromagnetic apparatus and method for the treatment of the inflammatory processes leading to neurological conditions of mental and behavioral conditions and disorders.

It is a further object of the invention to provide an electromagnetic apparatus and method for prophylactic use by a human or animal at risk for mental or behavioral conditions and disorders.

It is a further object of the invention to provide an electromagnetic apparatus and method to increase blood flow in an affected area.

It is yet another object to provide an apparatus for the application of the electromagnetic waveforms directly to the head area so as to easily and efficiently allow for the treatment of mental and behavioral conditions or disorders by using a portable generator that powers flexible coil applicator(s).

It is another object to provide an apparatus for the application of the electromagnetic waveforms directly to the head area so as to easily and efficiently allow for the treatment of mental and behavioral conditions or disorders by using a portable generator that powers flexible coil applicator(s) that are incorporated into or onto a flexible fabric, harness or other wearable to be worn during treatment.

It is another object of the invention to provide an apparatus delivering an inductive treatment for beneficial physiological effects through improvement of micro-vascular blood perfusion and reduced transudation.

It is a yet further object to provide an apparatus for use of an electromagnetic method of the character indicated, wherein operation of the apparatus can proceed at reduced power levels as compared to those of related methods known in electromedicine and respective biofield technologies, with attendant benefits of safety, economics, portability, and reduced electromagnetic interference.

According to an exemplary embodiment of the invention. a behavioral treatment device comprises one or more loop coils disposed in a wearable assembly that places the one or more loop coils proximate a head of a pet animal, such as a dogs or a cat. The one or more loop coils are coupled to a signal generator in order to emit an electromagnetic field, the signal generator being programmable to control the emitted electromagnetic field to conform to one or more predetermined treatment regimes for treating one or more of the following conditions in the pet animal (e.g., dogs, cats, etc.): Separation Anxiety; Thunder Phobia/Noise Sensitivity;

Travel Anxiety; Situational Anxiety (e.g. veterinary visits, strangers); General Anxiety; Geriatric Cognitive Impairment/Dysfunction; Phobias (Fears); OCD (Obsessive Compulsive Disorder) Related Behaviors; Aggression (secondary to fear or phobias); Depression.

According to an exemplary embodiment of the invention. a behavioral treatment device comprises one or more loop coils disposed in a wearable assembly that places the one or more loop coils proximate a head of a working animal, such as a horse. The one or more loop coils are coupled to a signal generator in order to emit an electromagnetic field, the signal generator being programmable to control the emitted electromagnetic field to conform to one or more predetermined treatment regimes for treating one or more of the following conditions in the working animal (e.g., horse): General Anxiety; Separation Anxiety (when separated from the herd); Travel Anxiety; Situational Anxiety; Cognitive Dysfunction; Phobias (fears); OCD (stall walking; weaving, cribbing); Depression.

According to an exemplary embodiment of the invention, a behavioral treatment device comprises a signal generator circuit coupled to a loop coil signal applicator, the signal generator circuit being configurable to generate a signal that comprises bursts of between 15-40 MHz sinusoidal waves, wherein the bursts repeat at between 0.01 and 100 Hz; the signal being transmitted as a pulsed electromagnetic field through the loop coil signal applicator to a treatment target region within the skull of a treatment subject, wherein the pulsed electromagnetic field has a strength of 200 milli-Gauss or less.

It is intended that any other advantages and objects of the present invention that become apparent or obvious from the detailed description, drawings or illustrations contained herein are within the scope of the present invention.

The above and yet other objects and advantages of the present invention will become apparent from the hereinafter set forth Brief Description of the Drawings and Detailed Description of the Invention.

BRIEF DESCRIPTION OF THE DRAWINGS

Preferred embodiments of the present invention will be described below in more detail, with reference to the accompanying drawings.

DETAILED DESCRIPTION OF THE INVENTION

Induced time-varying currents from PEMF or PRF devices flow in a target pathway structure, such as a molecule, cell, tissue, and organ, and it is these currents that are a stimulus to which cells and tissues can react to in a physiologically meaningful manner. It has been established that mental and behavioral conditions and disorders in humans and animals have underlying physiological, cellular, and biochemical components. The electrical properties of a target pathway structure affect levels and distributions of induced current. Molecules, cells, tissue, and organs are all in an induced current pathway, such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes, such as membrane transport.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency ($=2\pi f$, where f is frequency), $i=-1^{1/2}$, $Z_b(\omega)$ is the binding impedance and $R_{ion}$ and $C_{ion}$ are equivalent binding resistance and capacitance of an ion binding pathway. The value of the equivalent binding time constant, $\tau_{ion}=R_{ion}C_{ion}$, is related to an ion binding rate constant, $k_b$, via $\tau_{ion}=R_{ion}C_{ion}=1/k_b$. Thus, the characteristic time constant of this pathway is determined by ion binding kinetics.

Induced E from a PEMF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to the surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PEMF waveform to match a bandpass of target pathway structures. This allows for a required range of frequencies for any given induced E waveform for optimal coupling to target impedance, such as bandpass.

$Ca^{2+}$ binding to calmodulin ("CaM") is a frequent EMF target. Use of this pathway is based upon reports that acceleration of wound repair and for example bone repair, involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis is also integral to wound repair and modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ may then be employed in a cell array model to evaluate SNR by comparing voltage induced by a PRF signal to thermal fluctuations in voltage at a CaM binding site. Employing numerical values for PMF response, such as Vmax=6.5× 10−7 sec 1, $[Ca^{2+}]$=2.5 μM, KD=30 μM, $[Ca^{2+}CaM]$=KD $([Ca^{2+}]+[CaM])$, yields $k_b$=665 sec−1 ($\tau_{ion}$=1.5 msec). This value for $\tau_{ion}$ can be employed in an electrical equivalent circuit for ion binding while power SNR analysis may be performed for any waveform structure. In a preferred embodiment of the present invention a PEMF signal of 27.12 MHz with a pulse duration of 2 msec at 7 Hz is applied to the treatment area to effectuate the treatment of mental and behavioral conditions and disorders, in particular anxiety.

Figure 1:
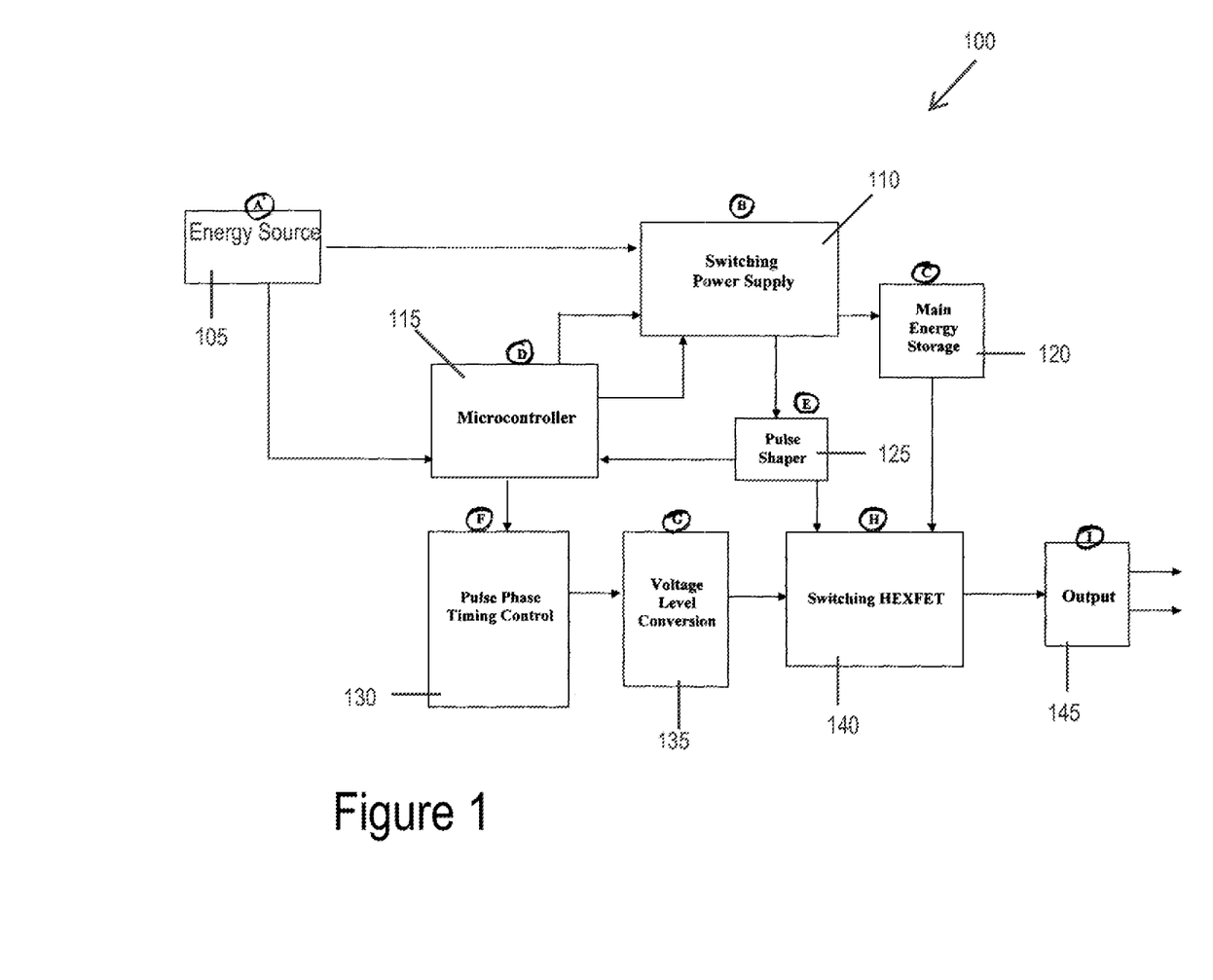
FIG. 1 is a block diagram of miniaturized circuitry according to a preferred embodiment of the present invention.

FIG. 1 depicts a block diagram of a miniature control circuit (hereinafter "portable generator," "waveform generator," or "generator) 100 for generating a signal to be transmitted as a PEMF treatment signal through an applicator coil to a treatment target according to an exemplary embodiment of the present invention. The miniature control circuit 100 produces waveforms that are driven through a transmitting device, such as one or more wire coils (hereinafter "applicator coil(s)," "loop(s)," "coil(s)"), for transmission to a treatment target, as will be described in further detail below. The miniature control circuit 100 has a self-contained energy source 105, which may be a replaceable or rechargeable battery. A preferred embodiment of the self-contained energy source 105 has an output voltage of 3.3 V but other voltages can be used. A switching power supply 110 controls voltage to a microcontroller 115. A preferred embodiment of the microcontroller 115 is an 8-bit 4 MHz microcontroller but other bit MHz combination micro-controllers may be used. The switching power supply 110 also delivers current to a main energy storage 120, which may be embodied by one or more storage capacitors. A preferred embodiment of the present invention uses storage capacitors having a 220 μF output but other outputs can be used. The storage capacitors of main energy storage 120 allow high frequency pulses to be delivered to a coupling device, such as inductors. The microcontroller 115 also controls a pulse shaper 125 and a pulse phase timing control 130. The pulse shaper 125 and pulse phase timing control 130 determine pulse shape, burst width, burst envelope shape, and burst repetition rate of an output signal. A voltage level conversion sub-circuit 135 controls an induced field delivered to a target pathway structure. A switching Hexfet 140 allows pulses of pseudo-randomized amplitudes to be delivered to an output 145 that routes a waveform to at least one delivery device, such as an inductor. The microcontroller 115 can also control total exposure time of a single treatment of a target pathway structure, such as a molecule, cell, tissue, and organ. A preferred embodiment according to the present invention uses treatments times of about 1 minute to about 30 minutes.

According to an exemplary embodiment of the invention, generator circuit 100 is configurable by Signal to Noise Ratio ("SNR") and Power Signal to Noise Ratio ("Power SNR") approaches to configure bioeffective waveforms.

Specifically, broad spectral density bursts of electromagnetic waveforms, configured to achieve maximum signal power within the bandpass of a biological target, are selectively applied to target pathway structures, such as living organs, tissues, cells and molecules. Waveforms are selected using a unique amplitude/power comparison with that of thermal noise in a target pathway structure. Signals comprise bursts of sinusoidal, rectangular, or pseudo-random wave shapes; have frequency content in a range of about 0.01 Hz to about 100 MHz at about 1 to about 100,000 wave shapes per second; and with a burst duration from about 0.01 to about 100 milliseconds; and a repetition rate from about 0.01 to about 1,000 bursts/second. Peak signal amplitude at a target pathway structure such as tissue, lies in a range of about 1 μV/cm to about 100 mV/cm. Each signal burst envelope may be a pseudo-random function providing a means to accommodate different electromagnetic characteristics of healing tissue. These waveforms may be delivered via inductive or capacitive coupling for 1 to 30-minute treatment sessions delivered according to predefined regimens by which PEMF treatment may be applied for 1 to 12 daily sessions, repeated daily. The treatment regimens for any waveform configured according to the instant invention may be fully automated or applied manually. The number of daily treatments may be programmed to vary on a daily basis according to any predefined protocol.

Figure 2:
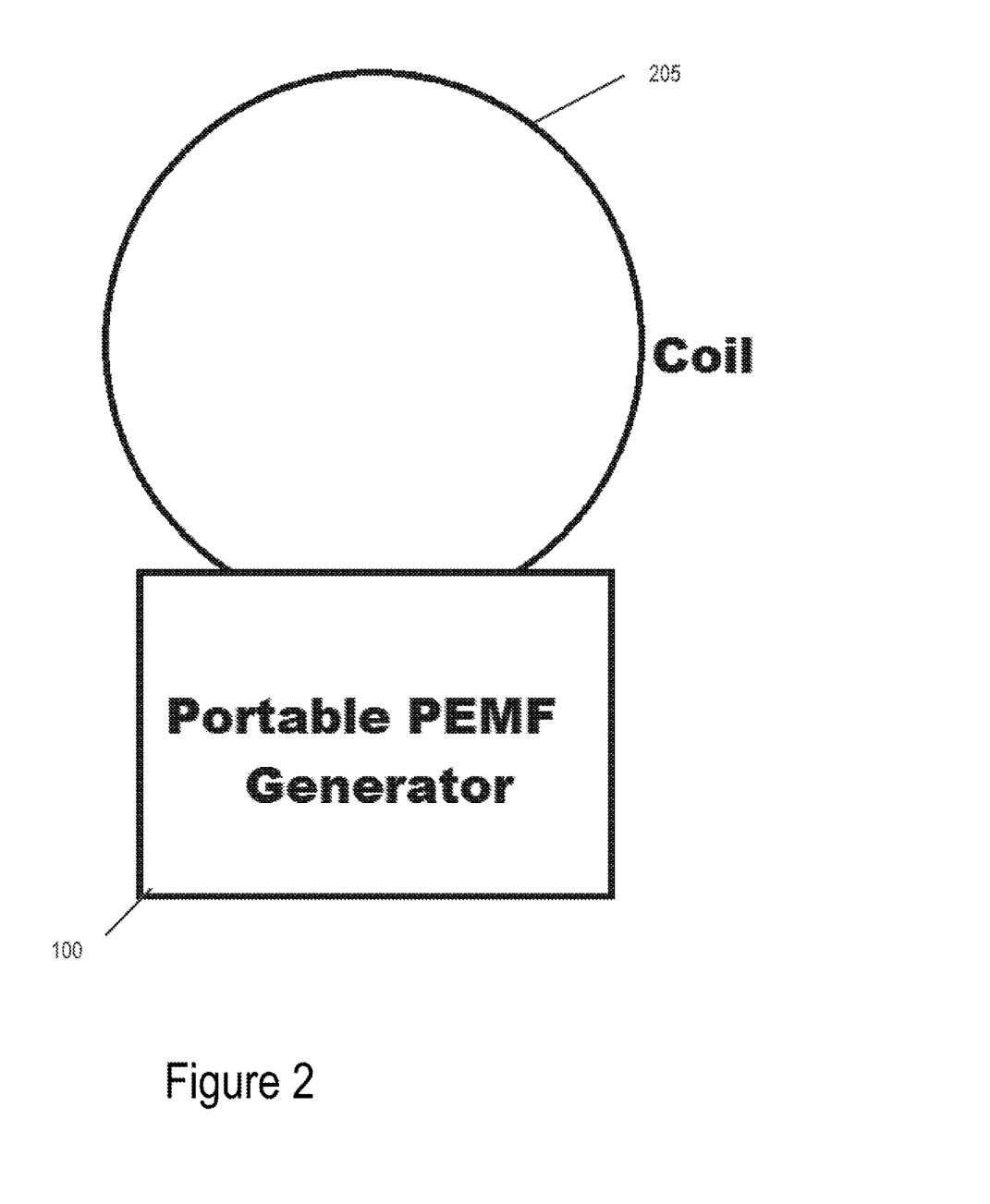
FIG. 2 depicts a drawing of a portable generator and coil according to a preferred embodiment of the present invention; and, FIG. 3 illustrates a preferred embodiment according to the present invention of an apparatus incorporating a harness for positioning the generator and applicator coil.

FIG. 2 depicts a drawing of a portable generator 100 and an applicator coil 205 according to an exemplary embodiment of the present invention. The applicator coil 205, comprising one or more turns of electrically-conductive wire in a generally circular or oval shape, is connected to a waveform generator 100 having circuitry generally configured as described above with reference to FIG. 1. The coil 205 can have circular dimensions ranging from about 2 inches in diameter to about 30 inches in diameter. The coil 205 may be conformed to a particular anatomical location, for example the head area of a human or animal. In a preferred embodiment of the present invention, there are two coil diameters of 5 inches and 7 inches used in accordance with the subject's head size.

Figure 3:
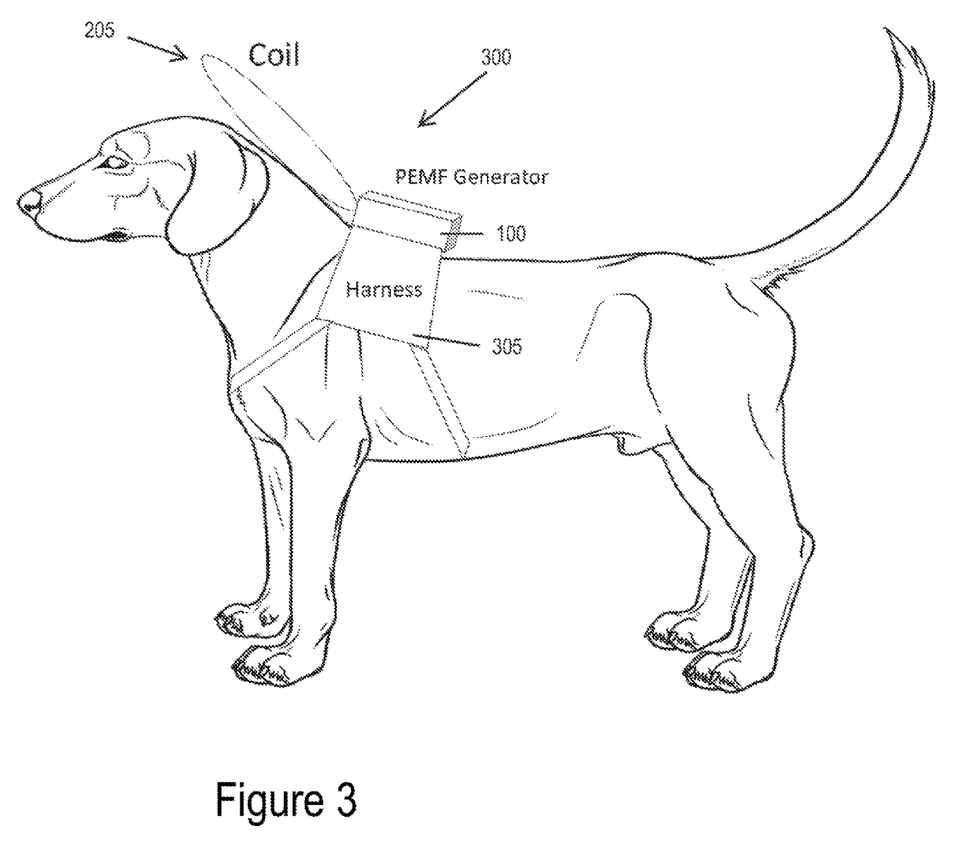

FIG. 3 illustrates a wearable assembly 300 incorporating portable generator 100 and applicator coil 205 for applying treatment to an animal according to an exemplary embodiment of the present invention. A supporting device 305, such as a harness, is worn to position the applicator coil 205 above the head of a human or animal. The harness 305 may be made of cotton, nylon, elastic or any other anatomical wrap or support material. The applicator coil 205 is positioned on the harness 305 such that the PEMF signal of the present invention is applied to the entire volume of the head for the treatment of mental or behavioral conditions or disorders, which result from neurological inflammatory processes or other contributing biophysiological, biochemical or neural factors. The PEMF Generator 100 is held in place on the support garment 305 using a fastening device, such as hook and loop, within a special pocket or by some other attachment so as to ease removal of the PEMF Generator 100 from the harness 305 by the user for cleaning, storage, replacement and other needs. The PEMF Generator 100 is coupled to the coil 205 by at least one connecting device, such as a flexible wire, or by emanating directly out of the enclosure of the generator 100—for example, as illustrated in FIG. 2.

Example 1

A preliminary study on pet animals was conducted on the efficacy of electromagnetic treatment on separation anxiety (SA) in pet dogs according to an exemplary embodiment of the invention. In particular, a number of pet dogs were subjected to daily treatments using a PEMF treatment apparatus conforming to wearable assembly 300 described above for a period of 42 days. Separation anxiety (SA), problematic behavior associated with anxiety that occurs exclusively in the owners' absence or perceived absence, is an important clinical issue in dogs affecting both their quality of life and their bond with their owners. Separation anxiety is a leading reason for owners abandoning their dogs, surrendering them to shelters or even euthanizing them. The condition is widespread, affecting an estimated 14% to 17% of households with dogs. Veterinarians rank it as the second most common behavioral disorder in dogs and in one recent VIN survey, 33% of respondent veterinarians reported that SA exists in over a quarter of their case load. While behavior modification and medications are used in combination to treat the majority of cases, treatment is often incomplete and unsatisfactory. Therefore, a significant unmet need exists for additional and effective treatment alternatives.

In particular, a treatment signal was selected in order to invoke anxiolytic effects and to inhibit proinflammatory cytokines or their signaling pathways. Corresponding to the description above, the strength of the treatment signal was selected so as to be sufficient to affect nervous system activity and cellular metabolism and signaling, but below the threshold required to directly induce action potentials. Finally, the subthreshold PEMF signal was selected to confirm positive effects of direct cranial stimulation with an induced electric field on cognitive disorders, such as depression, via changes in brain wave activity, including increase in theta wave activity associated with relaxation and anxiolytic responses.

The test subjects were selected in accordance with the following criteria:
 a. Dogs must be between 1-13 years of age, inclusive;
 b. Dogs must be generally healthy;
 c. Dogs must have a diagnosis of SA (from a veterinarian or behaviorist) for at least three months prior to enrollment;

Additionally, the subjects were selected according to the following criteria with respect to their owners:
 a. Owners must typically leave the dog alone upon their departure in an area where a 130 degree view videocamera can monitor their activity. This can be a large room, a section of a room, a crate or other confined space.
 b. Owner must provide a stable home environment for the duration of the study (9 weeks, including one week of baseline data collection, 6 weeks of treatment and 2 weeks of treatment withdrawal). A stable environment is defined as no major changes in the household routine (such as a single vacation of longer than 3 days; no more than 2 weekends away; no extended stay visitors; no arrival of new family members, including new pets, etc.).

Finally, potential subjects with one or more of the following conditions were excluded from the study:
 a. Dogs that are less than 1 year of age or older than 13 years of age
 b. Female dogs that are pregnant or lactating
 c. Dogs that have been recently diagnosed with SA (within the past 3 months)
 d. Dogs with a concomitant diagnosis of thunderstorm or noise phobia
 e. Dogs currently receiving psychoactive or sedating medication and whose dose has not been stable for the past month, at a minimum
 f. Dogs receiving more than one psychoactive or sedating medication, including episodic medications
 g. Dogs with concomitant conditions that are determined by the primary veterinarian or study investigator to potentially impact the study results A 7-day control period preceded a treatment period of 6 weeks (42 days) for 10 pet dogs, followed by a 2 week (14 days) treatment withdrawal period. Treatment progress was recorded for each animal at Day 7, Day 14, Day 28, Day 42, and Day 56, in the form of owner questionnaires and video recordings of the dogs when left home alone.

At the outset of the 7-day control (baseline) period, owners of the subjects were provided with a questionnaire to record an initial state of the test subjects:

TABLE 1

Separation Anxiety Symptom Severity Score

| Separation related behavior | 0 = absent  1 = mild  2 = moderate  3 = severe |
|---|---|
| Destructive behavior (chewing, breaking, tearing, etc.) includes crate | |
| Rearranging behavior (without destruction) | |
| Excessive Vocalization | |
| Inappropriate Urination | |
| Inappropriate Defecation | |
| Overall (Global) separation related anxiety | |

Table 1 above lists SA behaviors that were determined and noted by owners based on an owner leaving the pet animal for a prolonged period of at least 60 minutes, according to their established routine. Owners were asked to rate their dog's severity within each behavior listed as well as rate the dog's overall severity (global score), at baseline (Day −7 and Day 0) and periodically throughout the study (Day 7, 14, 28, 42 and 56). In addition to these owner assessments, dogs were recorded by video for 60 minutes in these sessions when the owner left the dog home alone. These videos were analyzed and the duration (percentage of time during the 60 minutes when the dog was engaged in the behavior) or for some behaviors the frequency (number of occurrences during the 60 minute video recording) of selected behaviors were noted and scored by the video analyzer. The behaviors that were analyzed in the videos included panting (PT); whining/howling (WH); urination; defecation; destruction (DE); rearranging (RA); orientation to the environment (OE); restlessness/pacing (RP); yawning; barking; and resting or passive behaviors (PA). The control period baseline was calculated for each dog on Day 0 as the percentage of time spent in the behavior during the first 60 minutes of video recording after the dog was left alone. For some behaviors, the number of occurrences of the behavior was counted instead of the duration. These included yawning, urination, defecation and barking.

Owner Questionnaires

For owner questionnaires, the respective negative behaviors were noted by the owners upon returning from the above-described separation periods of at least 60 minutes. The baseline was calculated as the scores provided by the owners on Day 0. Table 2 below shows recorded behavioral scores for 9 of the test animals on Day −7 and Day 0—i.e., the control period preceding treatment:

TABLE 2

|  | Day 0 | | | | |
|---|---|---|---|---|---|
| Day -7 | 0 | 1 | 2 | 3 | Total |
| 0 | 0 | 0 | 0 | 0 | 0 |
| 1 | 0 | 1 | 2 | 0 | 3 |
| 2 | 0 | 0 | 3 | 0 | 3 |
| 3 | 0 | 0 | 0 | 3 | 3 |
| Total | 0 | 1 | 5 | 3 | 9 |

As shown above, a subset of the 9 subjects exhibited an increase in behavioral issues during the control period—i.e., from day −7 to day 0 of the treatment testing period. In particular, two subjects moved from a score of 1 on Day −7 to a score of 2 on Day 0. The other subjects exhibited no changes in behavior over the same control period. In other words, none of the subjects showed any improvement in behavior over the control period. In addition to the above five (5) behavior-specific scores and one (1) overall score, each subject was also associated with up to 3 unique behaviors (CSOM).

Starting from Day 0, each subject was given two 15-minute treatments each day, spaced 8-10 hours apart, using an apparatus conforming to wearable assembly 300 described above and illustrated in FIG. 3. The center of coil 205 was placed over the base of each dog's skull, with the coil 205 either resting on the dog's skin or held slightly above it. The treatments were given at approximately the same time each day and well before planned times that the subjects' owners were to leave their homes (i.e., while the dog was still calm and not exhibiting anxiety related to anticipation of an owner's departure) For this example, the signal generator 100 was configured to produce a 7 Hz signal burst with a 27.12 MHz carrier frequency, the bursts being 2 ms in duration with a peak amplitude of 0.05 Gauss.

A positive response to treatment was seen as early as Day 7. As reflected in Table 3 below, from Day 0 to Day 7, five of the ten patients saw a reduction of at least one point in their overall scores. One of those patients saw a reduction of two points in their overall score (moving from a 2 to a 0). Four saw no change.

TABLE 3

|  | Day 7 | | | | |
|---|---|---|---|---|---|
| Day 0 | 0 | 1 | 2 | 3 | Total |
| 0 | 0 | 0 | 0 | 0 | 0 |
| 1 | 0 | 1 | 0 | 0 | 1 |
| 2 | 1 | 2 | 2 | 0 | 5 |
| 3 | 0 | 0 | 2 | 1 | 3 |
| Total | 1 | 3 | 4 | 1 | 9 |

As reflected in Table 4 below, from Day 0 to Day 14, six of the nine patients saw a reduction of at least one point in their overall scores. One of those patients saw a reduction of two points in their overall score (moving from a 2 to a 0). Three patients saw no change.

TABLE 4

|  | Day 14 | | | | |
|---|---|---|---|---|---|
| Day 0 | 0 | 1 | 2 | 3 | Total |
| 0 | 0 | 0 | 0 | 0 | 0 |
| 1 | 0 | 1 | 0 | 0 | 1 |
| 2 | 1 | 2 | 2 | 0 | 5 |
| 3 | 0 | 0 | 3 | 0 | 3 |
| Total | 1 | 3 | 5 | 0 | 9 |

As reflected in Table 5 below, from Day 0 to Day 28, nine of the nine patients saw a reduction of at least one point in their overall scores. One of those patients saw a two-point reduction (from 3 to 1). The patient that saw a reduction from 2 to 0 earlier was back at a 1 this week.

TABLE 5

|  | Day 28 | | | | |
|---|---|---|---|---|---|
| Day 0 | 0 | 1 | 2 | 3 | Total |
| 0 | 0 | 0 | 0 | 0 | 0 |
| 1 | 1 | 0 | 0 | 0 | 1 |
| 2 | 0 | 5 | 0 | 0 | 5 |
| 3 | 0 | 1 | 2 | 0 | 3 |
| Total | 1 | 6 | 2 | 0 | 9 |

As reflected in Table 6 below, from Day 0 to Day 42, nine of the nine patients saw at least a one-point reduction in their overall scores. Five of the nine patients saw a reduction to zero from their initial scores (one from one, three from two, and one from three). Five of the nine patients saw at least a two-point reduction.

TABLE 6

|  | Day 42 | | | | |
|---|---|---|---|---|---|
| Day 0 | 0 | 1 | 2 | 3 | Total |
| 0 | 0 | 0 | 0 | 0 | 0 |
| 1 | 1 | 0 | 0 | 0 | 1 |
| 2 | 3 | 2 | 0 | 0 | 5 |
| 3 | 1 | 1 | 1 | 0 | 3 |
| Total | 5 | 3 | 1 | 0 | 9 |

As reflected in Table 7 below, from Day 0 to Day 56, three of the nine dogs were back at a score of two. Six remain in lower score categories on Day 56 when compared to Day 0.

TABLE 7

|  | Day 56 | | | | |
|---|---|---|---|---|---|
| Day 0 | 0 | 1 | 2 | 3 | Total |
| 0 | 0 | 0 | 0 | 0 | 0 |
| 1 | 1 | 0 | 0 | 0 | 1 |
| 2 | 2 | 0 | 3 | 0 | 5 |
| 3 | 1 | 1 | 1 | 0 | 3 |
| Total | 4 | 1 | 1 | 0 | 9 |

In other words, three of the subjects showed some regression approximately two weeks after treatments were stopped.

Table 8 below lists, for each progress record date, a percentage (%) of success (1 point reduction overall) and a confidence interval for the recorded success (wald score interval if 100%)

TABLE 8

| Days | Number of Dogs | Proportion of Successes | 95% Confidence Interval |
|---|---|---|---|
| 0 to 7 | 9 | 0.56 | (0.21, 0.86) |
| 0 to 14 | 9 | 0.67 | (0.29, 0.93) |
| 0 to 28 | 9 | 1.00 | (0.66, 1.00) |
| 0 to 42 | 9 | 1.00 | (0.66, 1.00) |
| 0 to 56 | 9 | 0.67 | (0.29, 0.93) |

Table 9 below lists, for each progress record date, a percentage (%) complete resolution of all behavioral issues (reach 0) by Day 56, side by side with success rate shown in Table 8.

TABLE 9

| Days | Number of Dogs | Proportion of Successes | 95% Confidence Interval | Proportion Resolved | 95% Confidence Interval |
|---|---|---|---|---|---|
| 0 to 7 | 9 | 0.56 | (0.21, 0.86) | 0.11 | (0.00, 0.48) |
| 0 to 14 | 9 | 0.67 | (0.29, 0.93) | 0.11 | (0.00, 0.48) |
| 0 to 28 | 9 | 1.00 | (0.66, 1.00) | 0.11 | (0.00, 0.48) |
| 0 to 42 | 9 | 1.00 | (0.66, 1.00) | 0.56 | (0.21, 0.86) |
| 0 to 56 | 9 | 0.67 | (0.29, 0.93) | 0.44 | (0.13, 0.79) |

Correspondingly, the percentages of success and percentages of complete resolution were recorded for each of the five (5) tested common behaviors, as listed in Table 1 above. It was noted that some of the high instances of resolved behaviors were because some of the subjects started at a zero in those specific behaviors.

Inappropriate Defecation:
All nine dogs in the study started at zero and remained at zero for inappropriate defecation.

Destructive Behavior:
Table 10 below lists the results for destructive behavior and Table 11 lists the results for a subset of the subjects that showed a non-zero score for this behavior at Day 0.

TABLE 10

Behavior: Destruct (Note: Five of the nine dogs started at zero for the resolved proportions)

| Days | Number of Dogs | Proportion of Successes | 95% Confidence Interval | Number of Dogs | Proportion Resolved | 95% Confidence Interval |
|---|---|---|---|---|---|---|
| 0 to 7 | 9 | 0.11 | (0.00, 0.48) | 9 | 0.55 | (0.21, 0.86) |
| 0 to 14 | 9 | 0.11 | (0.00, 0.48) | 9 | 0.55 | (0.21, 0.86) |
| 0 to 28 | 9 | 0.33 | (0.07, 0.70) | 9 | 0.55 | (0.21, 0.86) |
| 0 to 42 | 9 | 0.44 | (0.13, 0.79) | 9 | 0.78 | (0.39, 0.97) |
| 0 to 56 | 9 | 0.44 | (0.13, 0.79) | 9 | 0.67 | (0.29, 0.93) |

TABLE 11

Behavior: Destruct (Only for the non-zero dogs)

| Days | N | Proportion of Successes | 95% Confidence Interval | N | Proportion Resolved | 95% Confidence Interval |
|---|---|---|---|---|---|---|
| 0 to 7 | 4 | 0.25 | (0.00, 0.81) | 4 | 0.00 | NA |
| 0 to 14 | 4 | 0.25 | (0.00, 0.81) | 4 | 0.00 | NA |
| 0 to 28 | 4 | 0.75 | (0.19, 0.99) | 4 | 0.00 | NA |
| 0 to 42 | 4 | 1.00 | (0.39, 1.00) | 4 | 0.50 | (0.06, 0.93) |
| 0 to 56 | 4 | 1.00 | (0.39, 1.00) | 4 | 0.50 | (0.06, 0.93) |

Rearranging Behavior:
Table 12 below lists the results for rearranging behavior and Table 13 lists the results for a subset of the subjects that showed a non-zero score for this behavior at Day 0.

TABLE 12

Behavior: Rearrange (Note: Five of the ten dogs started at zero)

| Days | Number of Dogs | Proportion of Successes | 95% Confidence Interval | Number of Dogs | Proportion Resolved | 95% Confidence Interval |
|---|---|---|---|---|---|---|
| 0 to 7 | 9 | 0.11 | (0.00, 0.48) | 9 | 0.55 | (0.21, 0.86) |
| 0 to 14 | 9 | 0.22 | (0.02, 0.60) | 9 | 0.55 | (0.21, 0.86) |
| 0 to 28 | 9 | 0.44 | (0.13, 0.79) | 9 | 0.55 | (0.21, 0.86) |
| 0 to 42 | 9 | 0.44 | (0.13, 0.79) | 9 | 0.78 | (0.39, 0.97) |
| 0 to 56 | 9 | 0.22 | (0.02, 0.60) | 9 | 0.67 | (0.29, 0.93) |

TABLE 13

| | | | Behavior: Rearrange (Only for the non-zero dogs) | | | |
|---|---|---|---|---|---|---|
| Days | N | Proportion of Successes | 95% Confidence Interval | N | Proportion Resolved | 95% Confidence Interval |
| 0 to 7 | 4 | 0.25 | (0.00, 0.81) | 4 | 0.00 | NA |
| 0 to 14 | 4 | 0.50 | (0.06, 0.93) | 4 | 0.00 | NA |
| 0 to 28 | 4 | 1.00 | (0.39, 1.00) | 4 | 0.00 | NA |
| 0 to 42 | 4 | 1.00 | (0.39, 1.00) | 4 | 0.50 | (0.06, 0.93) |
| 0 to 56 | 4 | 0.50 | (0.06, 0.93) | 4 | 0.25 | (0.00, 0.81) |

Inappropriate Urination:

Eight of the nine dogs started at zero. The dog that did not start at zero started at a two and moved to a zero by Day 7, moved back to a two at Day 28, returned to zero at Day 42, and remained at zero through Day 56. Of the eight dogs that started at zero at Day 0, one moved to one at Day 56.

Excessive Vocalization:

Table 14 below lists the results for excessive vocalization and Table 15 lists the results for a subset of the subjects that showed a non-zero score for this behavior at Day 0.

TABLE 14

| | | | Behavior: Vocalize (Note: Two of these dogs started at zero) | | | |
|---|---|---|---|---|---|---|
| Days | Number of Dogs | Proportion of Successes | 95% Confidence Interval | Number of Dogs | Proportion Resolved | 95% Confidence Interval |
| 0 to 7 | 8 | 0.63 | (0.24, 0.91) | 8 | 0.25 | (0.03, 0.65) |
| 0 to 14 | 9 | 0.56 | (0.21, 0.86) | 9 | 0.22 | (0.02, 0.60) |
| 0 to 28 | 9 | 0.89 | (0.51, 0.99) | 9 | 0.22 | (0.02, 0.60) |
| 0 to 42 | 9 | 0.88 | (0.51, 0.99) | 9 | 0.67 | (0.29, 0.93) |
| 0 to 56 | 9 | 0.67 | (0.29, 0.93) | 9 | 0.44 | (0.13, 0.79) |

TABLE 15

| | | | Behavior: Vocalize (Only for the non-zero dogs) | | | |
|---|---|---|---|---|---|---|
| Days | N | Proportion of Successes | 95% Confidence Interval | N | Proportion Resolved | 95% Confidence Interval |
| 0 to 7 | 7 | 0.71 | (0.29, 0.96) | 7 | 0.28 | (0.03, 0.71) |
| 0 to 14 | 8 | 0.63 | (0.24, 0.91) | 8 | 0.25 | (0.03, 0.65) |
| 0 to 28 | 8 | 1.00 | (0.63, 1.00) | 8 | 0.25 | (0.03, 0.65) |
| 0 to 42 | 8 | 1.00 | (0.63, 1.00) | 8 | 0.63 | (0.24, 0.91) |
| 0 to 56 | 8 | 0.75 | (0.34, 0.97) | 8 | 0.37 | (0.08, 0.75) |

In addition to the five (5) commonly-tested behaviors, again, each subject was associated with up to three (3) unique behaviors, which were recorded as CSOM scores for each progress record day (0, 7, 14, 28, 42, and 56). The same one-point difference from Day 0 standard was used to determine success. If the average was zero, the score was considered resolved.

TABLE 16

| | | | CSOM | | | |
|---|---|---|---|---|---|---|
| Days | Number of Dogs | Proportion of Successes | 95% Confidence Interval | Number of Dogs | Proportion Resolved | 95% Confidence Interval |
| 0 to 7 | 8 | 0.25 | (0.03, 0.65) | 8 | 0.00 | N/A |
| 0 to 14 | 9 | 0.22 | (0.02, 0.60) | 9 | 0.00 | N/A |
| 0 to 28 | 9 | 0.67 | (0.29, 0.93) | 9 | 0.00 | N/A |

TABLE 16-continued

| | | | CSOM | | | |
|---|---|---|---|---|---|---|
| Days | Number of Dogs | Proportion of Successes | 95% Confidence Interval | Number of Dogs | Proportion Resolved | 95% Confidence Interval |
| 0 to 42 | 9 | 0.78 | (0.39, 0.97) | 9 | 0.22 | (0.02, 0.60) |
| 0 to 56 | 9 | 0.56 | (0.21, 0.86) | 9 | 0.33 | (0.07, 0.70) |

From Day 42 to Day 56, 56% (5/9) of the dogs maintained their improvement (95% CI: (0.21, 0.86)). The overall maintenance of improvement over this treatment withdrawal period, as well as those specific to particular SA behaviors, is summarized in Table 17 below.

TABLE 17

| Behavior | Number of Dogs | Proportion Maintained (no deterioration from Day 42 to Day 56) | 95% Confidence Interval |
|---|---|---|---|
| Defecate | 9 | All zero at Day 0. | N/A |
| Destruct | 9 | 0.89 | (0.51, 0.99) |
| Rearrange | 9 | 0.78 | (0.39, 0.97) |
| Urinate (9 were zero at Day 0) | 9 | 0.89 | (0.51, 0.99) |
| Vocalize | 9 | 0.67 | (0.29, 0.93) |
| Overall | 9 | 0.56 | (0.21, 0.86) |
| CSOM | 9 | 0.56 | (0.21, 0.86) |

Video Recording

As described above, the subjects were recorded by video for 60 minutes when the owners left them home alone. These videos were analyzed and the duration (percentage of time during the 60 minutes when the dog was engaged in the behavior) or for some behaviors the frequency (number of occurrences during the 60 minute video recording) of selected behaviors were noted and scored by the video analyzer. The behaviors that were analyzed in the videos included panting (PT); whining/howling (WH); urination; defecation; destruction (DE); rearranging (RA); orientation to the environment (OE); restlessness/pacing (RP); yawning; barking; and resting or passive behaviors (PA). The control period baseline was calculated for each dog on Day 0 as the percentage of time spent in the behavior during the first 60 minutes of video recording after the dog was left alone. For some behaviors, the number of occurrences of the behavior was counted instead of the duration. These included yawning, urination, defecation and barking.

For negative behaviors (DE, RA, RP, OE, PT, WH), if the initial value (at Day 0) were zero, there could not have been any reduction. Accordingly, success indicators were set to zero for subjects that showed a null initial value. Otherwise, if the ratio of the final day (Day 28, 42, or 56) to the baseline day (Day 0 or −7) was less than 0.9, that behavior was considered an improvement and a success. If any behavior showed such a determined improvement, the dog was counted as an overall success.

Table 18 below lists the results related to the specific negative behaviors that were analyzed in the video recordings.

TABLE 18

| Behavior | #Dogs | Day 0 | Day 28 (% Δ) | Day 42 (% Δ) | Day 56 (% Δ) |
|---|---|---|---|---|---|
| Behaviors Scored by Duration - Total for all dogs with the behavior | | | | | |
| DE | 2 | 8 | 7.9 (−1.3%) | 16.4 (+105%) | 0.9 (−89%) |
| RA | 2 | 30.4 | 1.3 (−96%) | 4.6 (−85%) | 35.3 (+16%) |
| RP | 3 | 36.2 | 8.8 (−76%) | 11.7 (−67%) | 8.4 (−77%) |
| OE | 9 | 383.6 | 337.5 (−12%) | NA* | NA* |
| PT | 2 | 70.3 | 78.6 (+12%) | 82 (+17%) | 78.9 (+12%) |
| Behaviors Scored by Frequency of Occurrence -Total for All dogs with the behavior | | | | | |
| WH | 2 | 17.8 | 20.5 (+15%) | 9.6 (−54%) | 7.4 (−58%) |
| Barking | 4 | 1224 | 298 (−76%) | 1152 (−6%) | 36 (−97%) |
| Yawning | 0 | 0 | | | |
| Urination | 0 | 0 | | | |
| Defecation | 0 | 0 | | | |

*Video results from two dogs was not useable on Day 42; and one was not useable on Day 56

(Note: a (−) change indicates improvement and a (+) change indicates worsening of the behavior)

As reflected above in Table 18, some of the subjects showed significant improvements in DE, RP, WH, and barking at the end of the study (Day 56), while some of the subjects showed slight worsening in RA and PT.

Table 19 below lists the results of overall successes determined by analyzing the video recordings of the subjects.

TABLE 19

| Reduction in any one negative behavior | Number of Dogs | Percentage of Overall Successes | 95% Exact Confidence Interval |
| --- | --- | --- | --- |
| Day 28 | 9 | 100% | (66.37%, 100%) |
| Day 42 | 7 | 85.71% | (42.13%, 99.64%) |
| Day 56 | 8 | 87.50% | (47.35%, 99.68%) |

For the positive behavior (PA), if the initial value (at Day 0) were zero, there could not have been any ratio of an increase—i.e., indeterminate degree of improvement for comparison purposes. One of the subjects had all PA values at zero so this success indicator was set to No for this subject. Otherwise, if the ratio of the final day (Day 28, 42, or 56) to the baseline day (Day 0 or −7) was greater than 1.1, there had been a greater than 10% improvement in positive behavior and was considered a success. Table 20 below lists the results of positive behavior improvements determined by analyzing the video recordings of the subjects.

TABLE 20

| Increase in positive behavior | Number of Dogs | Percentage of Success | 95% Exact Confidence Interval |
| --- | --- | --- | --- |
| Day 28 | 9 | 33.33% | (7.49%, 70.07%) |
| Day 42 | 7 | 85.71% | (42.13%, 99.64%) |
| Day 56 | 8 | 57.50% | (47.35%, 99.68%) |

In addition to the above, analysis was also conducted on retention of success that was obtained by a subset of the subjects that showed improvement by Day 28. To retain success by Day 42, a dog had to show overall success (10% improvement in at least one behavior) by Day 28 and remain a success at Day 42. To retain success by Day 56, a dog had to show success (10% improvement in at least one behavior) by Day 42 and remain a success at Day 56. Table 21 below lists the results of this analysis.

TABLE 21

| Retain Overall Success | Number of Dogs | Percentage of Success | 95% Exact Confidence Interval |
| --- | --- | --- | --- |
| Day 42 | 7 | 85.71% | (42.13%, 99.64%) |
| Day 56 | 6 | 83.33% | (35.88%, 99.58%) |

As reflected in Table 21 above, seven (7) of the subjects obtained overall success by Day 28 and of them six (6) retained success at Day 42. Correspondingly, of the six (6) that retained success at Day 42, five (5) retained success at Day 56.

In view of the above, the preliminary testing showed that the inventive treatment regime was effective in reducing behavior problems in pet animals over treatment periods as short as 7 days and the positive effects lasted as long as 56 days—i.e., at the end of the treatment withdrawal period of the study.

Having described embodiments for an apparatus and a method for delivering electromagnetic signals to human, and animal molecules, cells, tissue and organs for therapeutic purposes, and in particular for the treatment of mental and behavioral conditions and disorders, it is noted that modifications and variations can be made by persons skilled in the art in light of the above teachings. It is therefore to be understood that changes may be made in the particular embodiments of the invention disclosed which are within the scope and spirit of the invention as defined by the appended claims.

The invention claimed is:

1. A method for treating separation anxiety in a dog, comprising:
   measuring duration and/or number of occurrences of one or more separation anxiety behaviors in a dog, wherein the one or more separation anxiety behaviors comprise one or more of destructive behavior, rearranging behavior, vocalization, restlessness, orienting to an environment, urination, defecation and yawning in the dog,
   positioning a flexible coil wire applicator of a lightweight wearable or stationary pulsed electromagnetic field (EMF) therapy device adjacent to a head of the dog to be treated; and
   applying a treatment regime from the therapy device,
   wherein the treatment regime comprises a plurality of bursts of an electromagnetic signal having a peak amplitude of less than about 200 milliGauss,
   wherein the plurality of bursts have an average duration of between about 0.5 msec and about 50 msec,
   wherein the plurality of bursts are repeated at between 0.01 and 100 Hz, and
   wherein the treatment regime is effective to treat separation anxiety in the dog, as assessed by a reduction in the one or more of destructive behavior, rearranging behavior, vocalization, restlessness, orienting to the environment, urination, defecation and yawning in the dog.

2. The method of claim 1, wherein the plurality of bursts comprise sinusoidal waves of between 15-40 MHz.

3. The method of claim 2, wherein the sinusoidal waves have a 27.12 MHz carrier frequency.

4. The method of claim 1, wherein the treatment regime has a treatment on-time of between about 5 minutes and 30 minutes, followed by a treatment off-time that is greater than about 30 minutes.

5. The method of claim 4, wherein the treatment on-time is 15 minutes.

6. The method of claim 4, wherein the treatment off-time is about 8 to 16 hours.

7. The method of claim 1, wherein the positioning comprises placing a center of the coil wire applicator over a base of a skull of the dog.

8. The method of claim 1, wherein the plurality of bursts are repeated at approximately 7 Hz.

9. The method of claim 1, wherein the average duration of the plurality of bursts is approximately 2 ms.

10. The method of claim 1, wherein the peak amplitude is approximately 0.05 Gauss.

11. The method of claim 1, wherein the treatment regime comprises a 7 Hz signal burst with a 27.12 MHz carrier frequency, the bursts being 2 ms in duration with a peak amplitude of 0.05 Gauss.

12. The method of claim 1, wherein the vocalization by the dog comprises one or more of barking, whining and howling.

13. The method of claim 1, wherein the restlessness in the dog comprises pacing.

14. The method of claim 1, wherein the one or more of separation anxiety behaviors comprises one or more of the destructive behavior, the rearranging behavior and the vocalization.

\* \* \* \* \*